(12) United States Patent
Naito (10) Patent No.: US 11,305,990 B2
(45) Date of Patent: Apr. 19, 2022

(54) PROCESSING METHOD

(71) Applicant: Ushio Denki Kabushiki Kaisha, Tokyo (JP)

(72) Inventor: Keisuke Naito, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 246 days.

(21) Appl. No.: 16/485,734

(22) PCT Filed: Feb. 27, 2018

(86) PCT No.: PCT/JP2018/007117
§ 371 (c)(1),
(2) Date: Aug. 13, 2019

(87) PCT Pub. No.: WO2018/168433
PCT Pub. Date: Sep. 20, 2018

(65) Prior Publication Data
US 2020/0002167 A1    Jan. 2, 2020

(30) Foreign Application Priority Data

Mar. 15, 2017  (JP) .............................. JP2017-050203

(51) Int. Cl.
*A61L 2/20* (2006.01)
*C01B 13/10* (2006.01)

(52) U.S. Cl.
CPC .............. *C01B 13/10* (2013.01); *A61L 2/202* (2013.01); *A61L 2202/122* (2013.01); *A61L 2202/14* (2013.01); *A61L 2209/212* (2013.01)

(58) Field of Classification Search
CPC . A61L 2/10; A61L 2/202; A61L 2/208; A61L 2/24; A61L 9/20; A61L 2202/122;
(Continued)

(56) References Cited

U.S. PATENT DOCUMENTS 6,391,259 B1 *  5/2002  Malkin ................... C01B 13/11
                                                          422/28
6,576,190 B1    6/2003  Park
(Continued)

FOREIGN PATENT DOCUMENTS

JP    H02-21868 A    1/1990
JP    H05-245190 A    9/1993
(Continued)

OTHER PUBLICATIONS

International Search Report issued in PCT/JP2018/007117; dated May 29, 2018.

(Continued)

*Primary Examiner* — Timothy C Cleveland
(74) *Attorney, Agent, or Firm* — Studebaker & Brackett PC (57) ABSTRACT

The present invention has as its object the provision of a processing method that can perform a sterilization process and a deodorization process utilizing ozone with high efficiency, without humidification of a target object.

A processing method of the present invention includes obtaining an ozone-containing gas by irradiating an ozone material gas with ozone generation light that does not include light in an ozone decomposition wavelength range and does include light having a wavelength of not more than 200 nm; and exposing a target object to the obtained ozone-containing gas in a low humidity condition having a relative humidity of not more than 55% to process the target object.

8 Claims, 5 Drawing Sheets

(58) Field of Classification Search
CPC .......... A61L 2202/14; A61L 2209/212; C01B 13/10
See application file for complete search history.

(56) References Cited

U.S. PATENT DOCUMENTS

| | | | |
|---|---|---|---|
| 10,596,285 B2* | 3/2020 | Naito | A61L 2/202 |
| 2004/0120850 A1* | 6/2004 | Kaiser | A61L 2/24 |
| | | | 422/22 |
| 2006/0104858 A1 | 5/2006 | Potember et al. | |
| 2009/0274577 A1* | 11/2009 | Sorensen | A61L 2/202 |
| | | | 422/28 |
| 2018/0230011 A1 | 8/2018 | Naito et al. | |

FOREIGN PATENT DOCUMENTS

| | | |
|---|---|---|
| JP | H11-178515 A | 7/1999 |
| JP | 2000-004782 A | 1/2000 |
| JP | 2000-070953 A | 3/2000 |
| JP | 2000-245816 A | 9/2000 |
| JP | 2001-321431 A | 11/2001 |
| JP | 2001-352956 A | 12/2001 |
| JP | 2003-512134 A | 4/2003 |
| JP | 2006-020669 A | 1/2006 |
| JP | 2009-131354 A | 6/2009 |
| JP | 4697625 B2 | 6/2011 |
| JP | 2017-043513 A | 3/2017 |
| WO | 2004/065293 A2 | 8/2004 |

OTHER PUBLICATIONS

An Office Action; "Notice of Reasons for Refusal", mailed by the Japanese Patent Office dated Jan. 12, 2021, which corresponds to Japanese Patent Application No. 2017-050203 and is related to U.S. Appl. No. 16/485,734; with English language translation.

The extended European search report issued by the European Patent Office dated Nov. 20, 2020, which corresponds to European Patent Application No. 18767772.9-1104 and is related to U.S. Appl. No. 16/485,734.

An Office Action; "Notice of Reasons for Refusal", mailed by the Japanese Patent Office dated Aug. 31, 2021, which corresponds to Japanese Patent Application No. 2017-050203 and is related to U.S. Appl. No. 16/485,734; with English language translation.

* cited by examiner

PROCESSING METHOD

TECHNICAL FIELD

The present invention relates to a processing method that performs a sterilization process and a deodorization process utilizing an ozone-containing gas that contains ozone. More specifically, the present invention relates to a processing method suitably used for processing moisture-phobic articles.

BACKGROUND ART

Conventionally, as one of processing methods for a sterilization process and a deodorization process (hereinafter also referred to as "sterilization and deodorization processing method"), a method utilizing ozone ($O_3$) having strong oxidation power is known.

As methods for generating ozone, there are known a discharge system in which ozone is generated by silent discharge such as creeping discharge in an atmosphere of an ozone material gas (for example, an oxygen ($O_2$)-containing gas such as air, in the concrete), a photochemical reaction system for generating ozone by irradiating the ozone material gas with ultraviolet rays and the like.

In the sterilization and deodorization processing method, the discharge-system ozone generation method is widely used.

To be more specific, as a kind of sterilization and deodorization processing method utilizing ozone obtained by the discharge-system ozone generation method, there is disclosed a method in which air constituting a room atmosphere and articles disposed in a room are designated as target objects, and the target objects are exposed to a mixture of an ozone-containing gas (ozone-containing air, in the concrete) and water droplets (moisture) (refer to Patent Literature 1).

In the sterilization and deodorization processing method described in Patent Literature 1, the air constituting the room atmosphere is taken into a duct. Ozone is generated in the duct by generating creeping discharge, and ozone-containing air that contains the generated ozone and water droplets (moisture) generated from a spray nozzle are mixed. The mixture of the ozone-containing air and the water droplets is fed from the duct into the room, to process (sterilization process or deodorization process) the air constituting the atmosphere of the room and the articles disposed in the room. In the sterilization and deodorization method, from the viewpoint of processing efficiency, the room fed with the mixture of the ozone-containing air and the water droplets, in other words, the room during the process is preferably at a high humidity, specifically, at a humidity of not lower than 80%.

As other sterilization and deodorization processing methods utilizing ozone, various methods utilizing ozone generated by ozone generation methods other than the discharge-system ozone generation method are proposed (for example, refer to Patent Literatures 2 and 3).

More specifically, Patent Literature 2 discloses a method for performing a sterilization process and a deodorization process using a deodorization processing device having ozone generation means that generates ozone by the photochemical reaction-system ozone generation method. In this method, air constituting an ambient atmosphere of the deodorization processing device is designated as a target object, and the target object is exposed to ozone-containing air containing ozone that has been generated by the ozone generation means to perform deodorization process. In this method, ozone is generated by irradiating an ozone material gas (oxygen-containing gas) with ultraviolet rays having a wavelength of 185 nm. Patent Literature describes that when the ozone material gas used in the ozone generation method contains a high proportion of moisture, an ozone generation ratio may be reduced.

Patent Literature 3 discloses a method for performing a sterilization process by mixing ozone generated by the photochemical reaction-system ozone generation method or the like into water, and exposing target objects to the obtained ozone mixed water. Patent Literature 3 describes that in this method, from the viewpoint of ozone generation efficiency, the humidity of the ozone material gas (oxygen-containing gas) used in the ozone generation method may preferably be not more than 60%.

As described above, in the conventional sterilization and deodorization processing method utilizing ozone, it is known that the ozone generation efficiency depends on the humidity of the ozone material gas (oxygen-containing gas), and when the target object is a gas, the humidity of the gas, and when the target object is not a gas but an article, the humidity of air constituting an ambient atmosphere of the target object and the like. However, the effects of the generation methods for ozone utilized in the process on the processing efficiency do not become apparent. In other words, in the conventional sterilization and deodorization processing method utilizing ozone, the relationship between the ozone generation methods and the processing efficiency is not considered.

As a method for a sterilization process, a method utilizing active oxygen is proposed too (for example, refer to Patent Literature 4).

More specifically, Patent Literature 4 discloses a method for performing a sterilization process using a sterilization processing device that includes oxygen feeding means for feeding an oxygen-containing gas into a chamber containing a target object, pressure reduction means for reducing the pressure of the inside of the chamber and an ultraviolet lamp disposed in the chamber. The sterilization processing device requires two types of lamps, as the ultraviolet lamp, i.e., an active oxygen generation lamp that emits ultraviolet rays in a vacuum ultraviolet range and an active oxygen decomposition lamp that emits ultraviolet rays in a range other than the vacuum ultraviolet range. As the active oxygen generation lamp, a lamp that emits both of ultraviolet rays in the vacuum ultraviolet range and ultraviolet rays in a range other than the vacuum ultraviolet range may be used. More specifically, a low-pressure mercury lamp whose main output light has wavelengths of 185 nm, 254 nm, 313 nm, 366 nm and the like has been used. As the active oxygen decomposition lamp, a low-pressure mercury lamp that emits only ultraviolet rays having longer wavelengths than 200 nm to the outside has been used.

In this method, instruments used in various fields, for example, in a medical field are designated as target objects. In this method, after the pressure of a chamber containing the target object is reduced, an oxygen-containing gas is fed into the chamber, while the active oxygen generation lamp is turned on for a predetermined time. After that, the active oxygen decomposition lamp is turned on to perform the sterilization process. In the course of the sterilization process, active oxygen (O.) is generated by absorption of the ultraviolet rays in the vacuum ultraviolet range (the ultraviolet rays having a wavelength of 185 nm, in the concrete) by oxygen ($O_2$) in the oxygen-containing gas. It is said that due to the instability of the active oxygen (O.), the active oxygen (O.) is sometimes bound to the active oxygen (O.)

and returns to oxygen ($O_2$) again, or the active oxygen (O.) sometimes reacts with oxygen ($O_2$) to generate ozone ($O_3$). Also it is said that when the ultraviolet rays having a wavelength of not more than 260 nm (the ultraviolet rays having a wavelength of 254 nm, in the concrete) from the active oxygen decomposition lamp is absorbed by ozone ($O_3$), the ozone ($O_3$) is decomposed to generate oxygen ($O_2$) and active oxygen (O.). From the viewpoint of the concentration of active oxygen (O.), it is said that the humidity of the inside of the chamber in the course of the sterilization process is preferably 20 to 50%.

Furthermore, in Patent Literature 4, the sterilization process is performed, while the target object is irradiated with light of the low-pressure mercury lamp by turning on the low-pressure mercury lamp in the chamber that is fed with pure oxygen and has a humidity of 20 to 50%, and so it has been revealed from experiment that a favorable sterilization effect can be obtained.

Thus, the sterilization processing method disclosed in Patent Literature 4 shows that the concentration of the active oxygen (O.) depends on the humidity of the oxygen-containing gas constituting the ambient atmosphere of the target object, but does not reveal the effect of the ozone ($O_3$) generated in the course of the sterilization process on the sterilization process.

In recent years, the importance of hygienic maintenance relating to the manufacture and sales of food and the like is increasing, and especially in imported processed food, the necessity of the sterilization process is increasing. Accordingly, there is a problem that subjecting powdered food and dried food to processing (a steam sterilization process or the like, in the concrete) in a high humidity condition requiring humidification has the risk of impairing flavor, fragrance and the like. Therefore, a method for subjecting the moisture-phobic articles such as powdered food and dried food to the sterilization process without having the detrimental effects of quality deterioration, for example, impairment of flavor, fragrance and the like, is required.

CITATION LIST

Patent Literature

Patent Literature 1: Japanese Patent No. 4697625
Patent Literature 2: Japanese Patent Application Laid-Open No. 2009-131354
Patent Literature 3: Japanese Patent Application Laid-Open No. 2000-070953
Patent Literature 4: Japanese Patent Application Laid-Open No. 2006-020669

SUMMARY OF INVENTION

Technical Problem

The inventors of the present invention have diligently studied processing methods utilizing ozone, and has found out that the state of processing varies depending on a method for generating the ozone utilized in processing. In other words, in the processing methods utilizing ozone, it has become apparent that a large difference occurs in processing efficiency depending on a humidity condition, more specifically processing efficiency depending on a relationship with an exposure amount to ozone between the case of selecting a photochemical reaction-system ozone generation method and the case of selecting a discharge-system ozone generation method. The "exposure amount to ozone" is a value represented by the product of the concentration of ozone in an atmosphere to which a target object is exposed and a total time of exposure.

The present invention has been made in view of the foregoing circumstances, and has as its object the provision of a processing method that can perform a sterilization process and a deodorization process utilizing ozone with high efficiency, without humidification of a target object.

Solution to Problem

A processing method of the present invention includes obtaining an ozone-containing gas by irradiating an ozone material gas with ozone generation light that does not include light in an ozone decomposition wavelength range and does include light having a wavelength of not more than 200 nm; and exposing a target object to the obtained ozone-containing gas in a low humidity condition having a relative humidity of not more than 55% to process the target object.

In the processing method of the present invention, the ozone generation light may preferably be light emitted from a xenon excimer lamp.

In the processing method of the present invention, the ozone-containing gas may preferably have a relative humidity of not more than 55%. In the processing method of the present invention, the relative humidity of the ozone-containing gas is more preferably not more than 30%, and particularly preferably not more than 20%.

In the processing method of the present invention, an environmental gas constituting an atmosphere of a target object existing space in which the target object is present may preferably have a relative humidity of not more than 55%. In the processing method of the present invention, the relative humidity of the environmental gas constituting the atmosphere of the target object existing space in which the target object is present is more preferably not more than 30%, and particularly preferably not more than 20%.

In the processing method of the present invention, the ozone-containing gas may preferably be fed into a target object existing space constituted by a conveying path through which the target object is conveyed, so that the target object is exposed to the ozone-containing gas in the conveying path.

In the processing method of the present invention, the ozone-containing gas may preferably be fed into the target object existing space, so that the target object is exposed to the ozone-containing gas in the target object existing space.

In the processing method of the present invention, the target object may preferably be a moisture-phobic article.

Advantageous Effects of Invention

According to the processing method of the present invention, the target object is exposed to the ozone-containing gas that is obtained by irradiating the ozone material gas with the ozone generation light that does not include the light in the ozone decomposition wavelength range and does include the light having the wavelength of not more than 200 nm. Thus, even if the ozone generation light is applied, the generated ozone is not decomposed, and a humidity condition does not largely interfere with a processing efficiency.

Therefore, the processing method of the present invention can perform a sterilization process and a deodorization process utilizing ozone with a high efficiency, without humidifying the target object. As a result, the processing method of the present invention can process a moisture-phobic article with a high efficiency, without having the detrimental effects of quality deterioration in the course of processing.

DESCRIPTION OF EMBODIMENTS

Embodiments of a processing method of the present invention will be hereinafter described.

The processing method of the present invention is a method for processing a target object utilizing ozone ($O_3$), and more specifically, is used for a sterilization process, a deodorization process or the like of a target object. In other words, the processing method of the present invention is a processing method (sterilization and deodorization processing method) for subjecting a target object to the sterilization process or the deodorization process.

In the processing method of the present invention, an article is designated as the target object, and a preferable concrete example of the target object is a moisture-phobic article. As specific examples of the moisture-phobic article, may be mentioned powdered food (green juice powder and the like, in the concrete), dried food (dried green onions, dried strips of radish and the like, in the concrete), spices, powdered medicines (oriental herb such as Kakkonto and the like, in the concrete) and the like.

In the processing method of the present invention, an ozone-containing gas is obtained by irradiating an ozone material gas with ozone generation light, and the target object is exposed to, in other words, makes in contact with the obtained ozone-containing gas (ozone) to process the target object. Namely, the processing method (sterilization and deodorization processing method) utilizes ozone generated by a photochemical reaction-system ozone generation method. The processing method is characterized in that the ozone generation light does not include light in a wavelength range of decomposing ozone (hereinafter referred to as "ozone decomposition wavelength range") and does include light (ultraviolet rays) having a wavelength of not more than 200 nm, and the exposure to the ozone-containing gas is performed in a low humidity condition having a relative humidity of not more than 55%.

The "ozone material gas" used herein refers to a gas containing at least oxygen. Air is a concrete example of the ozone material gas. The "light in a wavelength range of decomposing ozone" used herein refers to light (ultraviolet rays) in a wavelength range of 240 to 280 nm.

In the processing method of the present invention, the wavelength range of the ozone generation light is not more than 200 nm, and preferably includes 172 nm.

Since the ozone generation light is light having a wavelength of not more than 200 nm, oxygen contained in the ozone material gas is decomposed to generate ozone. More specifically, by irradiating an oxygen molecule with the ozone generation light, the oxygen molecule is decomposed (dissociated) to generate oxygen atoms. The oxygen atom is bound to another oxygen molecule, whereby ozone is generated. Since the ozone generation light is light having a wavelength of not more than 200 nm, the ozone material gas is not irradiated with light in the ozone decomposition wavelength range, and therefore the generated ozone is not decomposed due to the irradiation with the ozone generation light.

Since the ozone generation light contains light having a wavelength of 172 nm, the irradiation of the ozone material gas with the ozone generation light enables generating hydrogen peroxide ($H_2O_2$), which is a kind of active oxygen, at a high efficiency. Therefore, it is possible to obtain a high processing efficiency (a sterilization rate and a deodorization rate, in the concrete).

In the processing method according to the present invention, the exposure of the target object to the ozone-containing gas is performed in a low humidity condition having a relative humidity of not more than 55%, more specifically, in a processing atmosphere, i.e., a humidity condition in which a gas constituting an ambient atmosphere around the target object has a relative humidity of not more than 55%.

As a concrete method for exposing the target object to the ozone-containing gas in the low humidity condition, may be mentioned the following methods (1) and (2).

The following method (1) is used in, for example, a linear-type processing mechanism, while the following method (2) is used in, for example, a batch-type processing mechanism.

(1) A method in which the relative humidity of the ozone-containing gas is set at not more than 55%, and the target object is exposed to the ozone-containing gas (hereinafter also referred to as "feeding gas control method").

(2) A method in which an environmental gas (hereinafter also referred to as "processing environmental gas") constituting an atmosphere of a target object existing space into which the ozone-containing gas has been fed is set at not more than 55%, and the target object is exposed to the ozone-containing gas (hereinafter also referred to as "atmospheric gas control method").

In the atmospheric gas control method, an example of a concrete method for setting the relative humidity of the processing environmental gas at not more than 55% will be described.

First, in a state that the ozone-containing gas is not fed, the relative humidity of a space to be the target object existing space or an environmental gas, specifically, air (hereinafter also referred to as "pre-processing environmental air") constituting an atmosphere of the target object existing space is set at not more than 55%. Next, in an independently partitioned ozone generation space to which the pre-processing environmental air is to be fed, the pre-processing environmental air is irradiated with the ozone generation light to obtain an ozone-containing gas (ozone-containing air). The resulting ozone-containing gas is fed into a space to be the target object existing space or the target object existing space. As necessary, the target object is disposed in the space to which the ozone-containing gas has been fed. Therefore, the relative humidity of the processing environmental gas can be set at not more than 55%.

In the atmospheric gas control method, as another example of the concrete method for setting the relative humidity of the processing environmental gas at not more than 55%, may be mentioned a method for appropriately controlling, by humidity adjustment means, the relative humidity of the space to be the target object existing space in a state of being fed with the ozone-containing gas or the environmental gas constituting the atmosphere of the target object existing space.

Each of the relative humidity of the ozone-containing gas in the feeding gas control method and the relative humidity of the processing environmental gas in the atmospheric gas control method (the two types of relative humidity are hereinafter also collectively referred to as "exposure relative humidity") is set at not more than 55%, more preferably at not more than 30%, and especially preferably at not more than 20%.

Since the exposure relative humidity is not more than 55%, as is apparent from an experiment example described later, a high processing efficiency (a high sterilization rate and a high deodorization rate, in the concrete) can be obtained even when an exposure time (processing time) of the target object to the ozone-containing gas is short and the concentration of ozone in the ozone-containing gas is low. More specifically, an exposure amount to ozone, which is a value represented by the product of an exposure time of the target object to the ozone-containing gas and the concentration of ozone in the ozone-containing gas, in other words, a value referred to as a CT value is not more than 40, a high processing efficiency can be obtained as compared with a processing method (sterilization and deodorization processing method) utilizing ozone generated by a discharge-system ozone generation method.

When the exposure relative humidity is not more than 30%, as is apparent from the experiment example described later, a high processing efficiency can be obtained, irrespective of the exposure time of the target object to the ozone-containing gas and the concentration of ozone in the ozone-containing gas, as compared with the processing method (sterilization and deodorization processing method) utilizing ozone generated by the discharge-system ozone generation method. In particular, when the exposure relative humidity is not more than 20%, an extremely high processing efficiency can be obtained as compared with the processing method (sterilization and deodorization processing method) utilizing ozone generated by the discharge-system ozone generation method.

"CT value" used herein is an index representing a sterilization and inactivation effect, and the higher the CT value, the larger the sterilization and inactivation effect.

As the ozone material gas, air constituting an atmosphere outside the target object existing space, air constituting the target object existing space or compressed air or oxygen fed from a cylinder or the like is suitably used. More specifically, in performing the processing with the feeding gas control method, air constituting an atmosphere outside the target object existing space or compressed air or oxygen fed from a cylinder or the like is suitably used. On the contrary, in performing the processing with the atmospheric gas control method, air constituting the target object existing space is suitably used.

In the processing method of the present invention, an irradiation condition of the ozone material gas with the ozone generation light is appropriately determined in consideration of the type of the target object and the like.

As an example of the irradiation condition of the ozone material gas with the ozone generation light, the intensity of irradiation is, for example, 23.3 [mW/cm$^2$], and an irradiation time is, for example, 14.6 [msec].

In the processing method of the present invention, from the viewpoint of the processing efficiency (in the concrete, the sterilization rate and the deodorization rate), the ozone-containing gas obtained by the irradiation of the ozone material gas with the ozone generation light is preferably immediately used in the processing.

In the processing method of the present invention, the exposure time (processing time) of the target object to the ozone-containing gas is appropriately determined in accordance with the concentration of ozone in the ozone-containing gas, in consideration of the type of the target object, processing required of the target object and the like.

To be more specific, when processing required of the target object is an Escherichia coli sterilization process, the value (CT value) of the product of an ozone concentration [ppm] and the exposure time [min] of the target object to the ozone-containing gas is preferably not lower than 60, in the relationship of the ozone-containing gas with the ozone concentration.

In the processing method of the present invention, as an ozone generation light source for emitting the ozone generation light, a light source that does not emit light in the ozone decomposition wavelength range and does emit light in a wavelength of not more than 200 nm, and more specifically, a discharge lamp such as an excimer lamp or a rare gas fluorescent lamp, a light emitting device such as an LED device or an LD device or the like is used.

The ozone generation light source including the excimer lamp or the rare gas fluorescent lamp does not require large input power, as compared with a mercury lamp, to generate a large amount of ozone. Therefore, ozone can be generated at a high efficiency. Since the excimer lamp and the noble gas fluorescent lamp have lower calorific values than the mercury lamp, it is possible to suppress the decomposition (thermal decomposition) of the generated ozone due to the heat from the lamp, and there is no need to provide cooling means for suppressing an increase in the temperature of the ozone generation space due to the heat from the lamp. Furthermore, since the excimer lamp and the rare gas fluorescent lamp have constant luminous efficiencies independently of environmental temperature, it is possible to obtain expected luminous efficiency irrespective of the installation environment of an ozone generator.

When the ozone generation light source includes the LED device, the ozone generation light source has a configuration such that, for example, a plurality of LED elements are appropriately arranged on a heat dissipation substrate.

In the present invention, the "excimer lamp" used herein is a lamp that utilizes electric discharge (dielectric barrier discharge) generated by the application of a high frequency voltage of 50 Hz to several MHz through a dielectric, as described in Kogelschatz, Pure & Appl. Chem. Vol. 62, No. 9, 1990, pp. 1667-1674.

The "rare gas fluorescent lamp" is a lamp that has a tubular arc tube made of a dielectric material having transparency such as quartz glass, in which sealing portions are formed at both ends, for example, and in which the arc tube is filled with a rare gas such as xenon, argon or krypton, and a phosphor layer is formed on the inner periphery of the arc tube. A pair of external electrodes are provided along a tubular axial direction of the arc tube a distance apart from each other. In the rare gas fluorescent lamp, by the application of a high frequency voltage to the pair of external electrodes, electric discharge is formed between the pair of external electrodes in a state of the dielectric (a tubular wall of the arc tube made of quartz glass) interposed therebetween. As a result, rare gas excimer molecules are formed in the arc tube. Excimer rays are emitted by transitions of the rare gas excimer molecules to a ground state. Since the excimer rays excite a phosphor that constitutes the phosphor layer, ultraviolet rays are generated from the phosphor layer and emitted to the outside of the arc tube.

As a preferable concrete example of the ozone generation light source, may be mentioned a xenon excimer lamp that emits light having a center wavelength of 172 nm.

Figure 1:
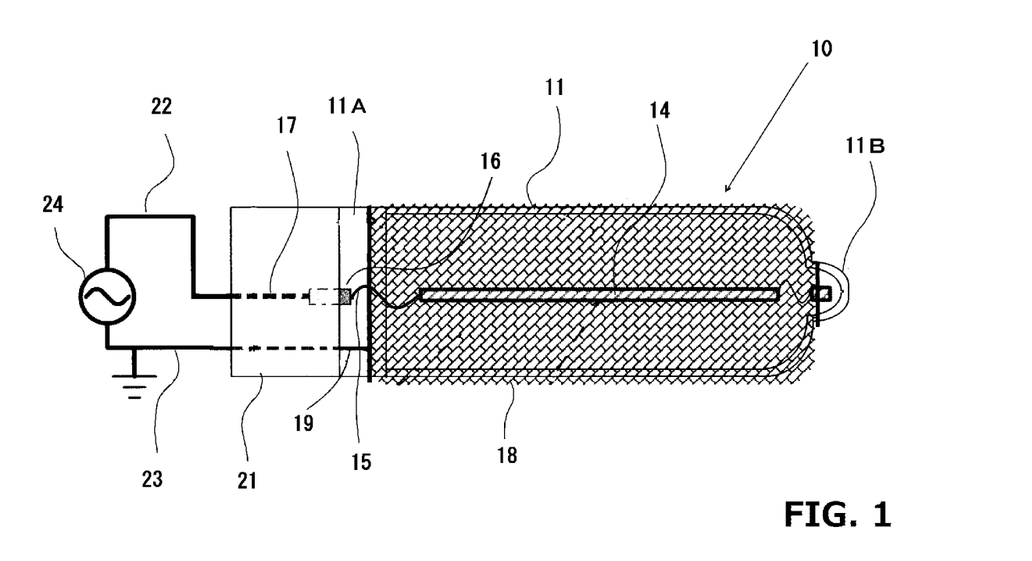
FIG. 1 is an explanatory view illustrating an example of a configuration of an excimer lamp, together with a base member and a high frequency power supply, used in a processing method of the present invention.

As shown in FIG. 1, an excimer lamp 10 is formed of an ultraviolet ray-transmitting material such as, for example, quartz glass, and is provided with a right cylindrical arc tube 11 in which one end (right end in FIG. 1) is sealed and a flat sealing portion 11A is formed at the other end (left end in FIG. 1) by pinch sealing. A rare gas such as a xenon gas is sealed within the arc tube 11, and a coil-shaped internal electrode 14 is disposed to extend along a tubular axis of the arc tube 11. The internal electrode 14 is electrically connected to a metal foil 16 embedded in the sealing portion 11A through an internal lead 15. The metal foil 16 is electrically connected to an end portion of an external lead for internal electrode 17, which protrudes from an external end surface of the sealing portion 11A to the outside. A mesh-shaped external electrode 18 is provided on an outer periphery of the arc tube 11. To the external electrode 18, an end portion of an external lead for external electrode 19 extending along the sealing portion 11A is electrically connected. A light-emitting area is formed in an area in which the internal electrode 14 and the external electrode 18 are opposed through an internal space of the arc tube 11 and a tube wall of the arc tube 11. Accordingly, a discharge space is formed within the arc tube 11.

A ceramic base member 21 is attached to the sealing portion 11A of the excimer lamp 10. Feeder lines 22 and 23 are provided in the base member 21. To the feeder lines 22 and 23, the other end portion of the external lead for external electrode 19 and the other end of the external lead for internal electrode 17 are connected, respectively.

In the excimer lamp 10, the internal electrode 14 is connected to a high frequency power supply 24 through the metal foil 16, the external lead for internal electrode 17 and the feeder line 22 of the base member 21, and the external electrode 18 is grounded through the external lead for external electrode 19 and the feeder line 23 of the base member 21.

In the illustrated example, the arc tube 11 has an exhaust pipe butt end 11B at its one end.

As concrete examples of the processing method of the present invention, may be mentioned methods using various processing mechanisms, as described later.

Which processing mechanism to use is appropriately selected in consideration of the type of a target object and the like.

Figure 2:
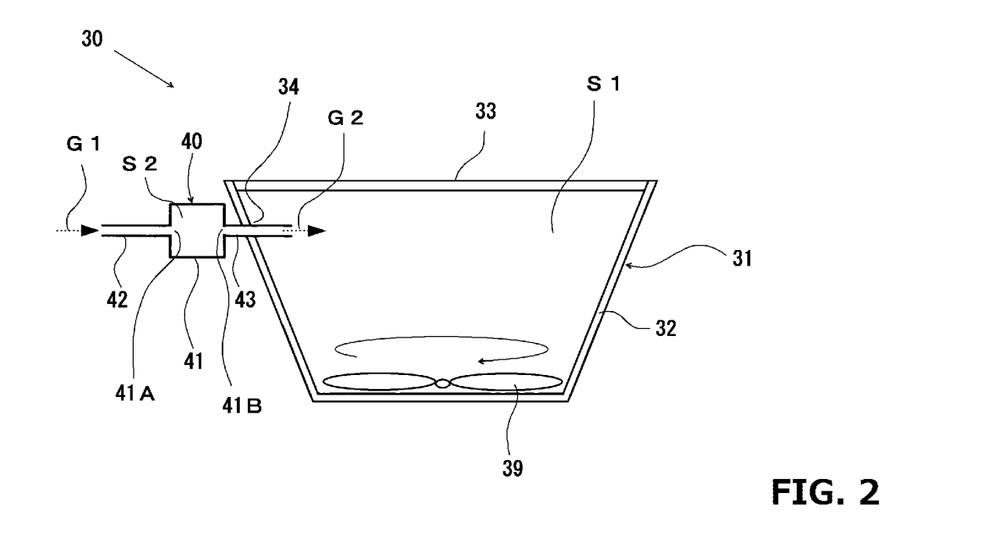
FIG. 2 is an explanatory view illustrating an example of a configuration of a processing mechanism used for implementing the processing method of the present invention.
Figure 3:
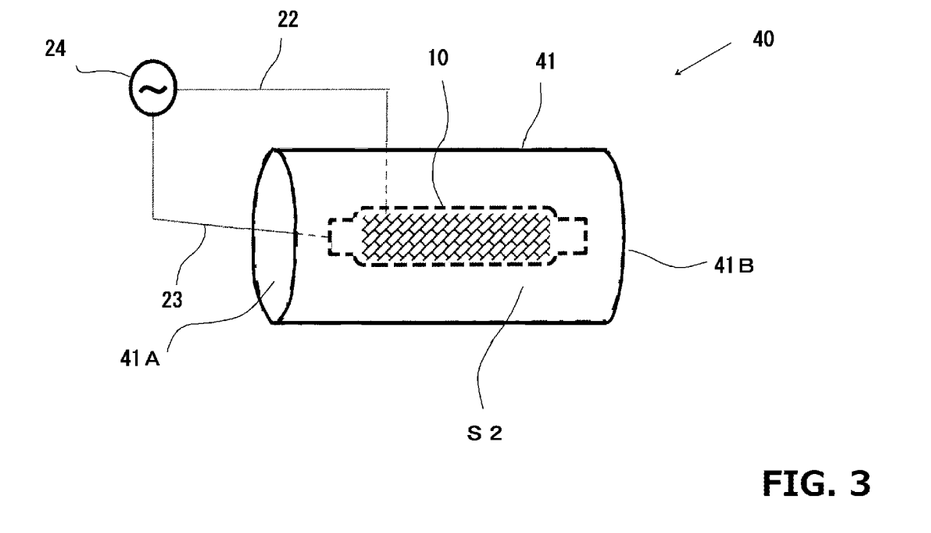
FIG. 3 is an explanatory view schematically illustrating an example of a configuration of an ozone generator in the processing mechanism of FIG. 2.

First Processing Mechanism:

FIG. 2 is an explanatory view illustrating an example of a configuration of a processing mechanism used for implementing the processing method of the present invention. FIG. 3 is an explanatory view schematically illustrating an example of a configuration of an ozone generator in the processing mechanism of FIG. 2.

In a first processing mechanism 30, a powdery moisture-phobic article is designated as a target object. The first processing mechanism 30 is a batch-type processing mechanism that includes a processing container 31 in which the target object is contained and processed, and an ozone generator 40 that includes an ozone generation light source and feeds an ozone-containing gas into the processing container 31. In the first processing mechanism 30, the processing container 31 is constituted of a container body 32 having an opening portion that opens upward, and a lid member 33 for opening and closing the opening portion. The processing container 31 is connected to the ozone generator 40 through a gas feed opening 34 formed in the container body 32. The internal space of the processing container 31 constitutes a processing space S1. In other words, the processing space S1 constitutes a target object existing space in which the target object is present. The first processing mechanism 30 performs processing in a state of enclosing the target object existing space, in other words, in a state of closing the opening portion between the internal space (processing space S1) of the processing container 31 and the outside (outside of the processing container 31) by the lid member 33.

In the example of the drawing, an agitator 39 for stirring the powdery moisture-phobic article (target object) is disposed in the processing container 31. In the processing container 31, there are provided humidity measurement means (not illustrated) for measuring the humidity of the processing space S1 (the relative humidity of an environmental gas constituting an atmosphere of the processing space S1, in the concrete), and humidity adjustment means (not illustrated) for controlling the humidity of the processing space S1 (the relative humidity of the environmental gas constituting the atmosphere of the processing space S1) to be not more than 55% on the basis of a value of the humidity (relative humidity) measured by the humidity measurement means.

In FIG. 2, a rotation direction of the agitator 39 is indicated by an arrow of a solid line.

The ozone generator 40 irradiates an ozone material gas G1 with ozone generation light to cause oxygen in the ozone material gas G1 to absorb the ozone generation light to generate ozone, and ejects an ozone-containing gas G2 containing the generated ozone to the outside of the ozone generator 40.

The ozone generator 40 includes a long right cylindrical flow path formation member 41. The cylindrical internal space of the flow path formation member 41 constitutes an ozone generation space S2. In the flow path formation member 41, an inlet 41A is formed at one end, and an outlet 41B is formed at the other end. Ozone material gas feeding means (not illustrated) is connected to the inlet 41A through an ozone material gas inlet path formed of a right cylindrical inlet path formation member 42. A right cylindrical outlet path formation member 43 is connected to the outlet 41B. The outlet path formation member 43 is airtightly inserted into the gas feed opening 34 formed in the container body 32. In the flow path formation member 41 (ozone generation space S2), the ozone generation light source including the excimer lamp 10 having the configuration of FIG. 1 is disposed such that the whole light-emitting area is situated in the inside of the flow path formation member 41 in such a state of being connected to the high frequency power supply 24 through the feeder line 22 and grounded through the feeder line 23. The excimer lamp 10 has a smaller external diameter than the internal diameter of the flow path formation member 41, and a shorter emission length (the length of the light-emitting area) than the whole length of the flow path formation member 41. The excimer lamp 10 is supported by a support member (not illustrated) in the inside of the flow path formation member 41 such that a tubular axis (lamp central axis) of the excimer lamp 10 approximately coincides with a tubular axis of the flow path formation member 41. In other words, the excimer lamp 10 is disposed such that the tubular axis (lamp central axis) approximately coincides with the tubular axis of the flow path formation member 41, and an outer periphery of the excimer lamp 10 is apart from an inner periphery of the flow path formation member 41 in the entire circumference so that a ring-shaped space is formed between the outer periphery and the inner periphery. Accordingly, an ozone material gas flow path through which the ozone material gas G1 fed from the ozone material gas feeding means through the inlet 41A flows to the outlet 41B is formed inside the flow path formation member 41 i.e. the ozone generation space S2.

The entire inner periphery of the flow path formation member 41 is resistant to ozone, and as necessary, blocks light from the ozone generation light source (excimer lamp 10). The flow path formation member 41 is preferably made of a material resistant to ozone, such as a fluorine resin or stainless steel.

In the inner periphery of the flow path formation member 41, at least an area that is irradiated with the light from the ozone generation light source preferably has light reflectivity of the ozone generation light.

Since the flow path formation member 41 has light reflectivity at the area that is irradiated with the light from the ozone generation light source, the light from the ozone generation light source (ozone generation light) can be effectively utilized, thus enabling generation of ozone with a high efficiency.

In the illustrated example, since the flow path formation member 41 is made of metal (SUS316, in the concrete), the entire inner periphery has resistant to ozone and light reflectivity, and blocks light from the excimer lamp 10.

As the ozone material gas feeding means, may be used air blowing means that can take air (ambient air) constituting an environmental atmosphere of the first processing mechanism 30 (outside atmosphere of the processing container 31 and the ozone generator 40, in the concrete) and can feed the air constituting the environmental atmosphere into the flow path formation member 41 (ozone generation space S2) to cause the air to flow therethrough.

A feeding condition of the ozone material gas G1 by the ozone material gas feeding means is appropriately determined in consideration of the internal diameter of the flow path formation member 41, the external diameter of the excimer lamp 10 and the like, such that the ozone material gas G1 is irradiated with the ozone generation light in a prescribed irradiation condition inside the flow path formation member 41 (ozone generation space S2).

In the first processing mechanism 30 having such configuration, a sterilization process is performed on the target object (powdery moisture-phobic article) present in the processing space S1 (target object existing space) by the atmospheric gas control method of the processing method of the present invention.

More specifically, in the ozone generator 40, the air (ambient air) constituting the environmental atmosphere of the first processing mechanism 30 is fed by the ozone material gas feeding means as the ozone material gas G1 from the inlet path formation member 42 (ozone material gas inlet path) through the inlet 41A into the flow path formation member 41 (ozone generation space S2). The ozone material gas G1 fed into the flow path formation member 41 flows through the ozone material gas flow path to the outlet 41B, and is irradiated with the light (ozone generation light) from the excimer lamp 10 (ozone generation light source). Oxygen in the ozone material gas G1 absorbs the ozone generation light (ultraviolet rays), and so ozone is generated by ozone generation reaction. In this manner, the ozone-containing gas G2 that contains ozone generated by the irradiation of the ozone material gas G1 with the ozone generation light is ejected to the outside of the ozone generator 40 from an ozone-containing gas outlet path constituted by the outlet path formation member 43 through the outlet 41B.

In the internal space (processing space S1) of the processing container 31 to which the ozone-containing gas G2 is fed in this manner, in other words, in the target object existing space, the agitator 39 stirs the powdery moisture-phobic article, and the humidity adjustment means sets the relative humidity of an environmental gas (processing environmental gas) constituting the atmosphere of the target object existing space at not more than 55%.

In this manner, the target object present in the target object existing space is exposed to the ozone-containing gas G2 fed from the ozone generator 40 (ozone generation space S2) into the target object existing space at a low humidity condition, to subject the target object to a sterilization process. During the process, the powdery moisture-phobic article is kept in a stirred condition by the agitator 39, and the target object existing space is continuously fed with the ozone-containing gas G2.

Figure 4:
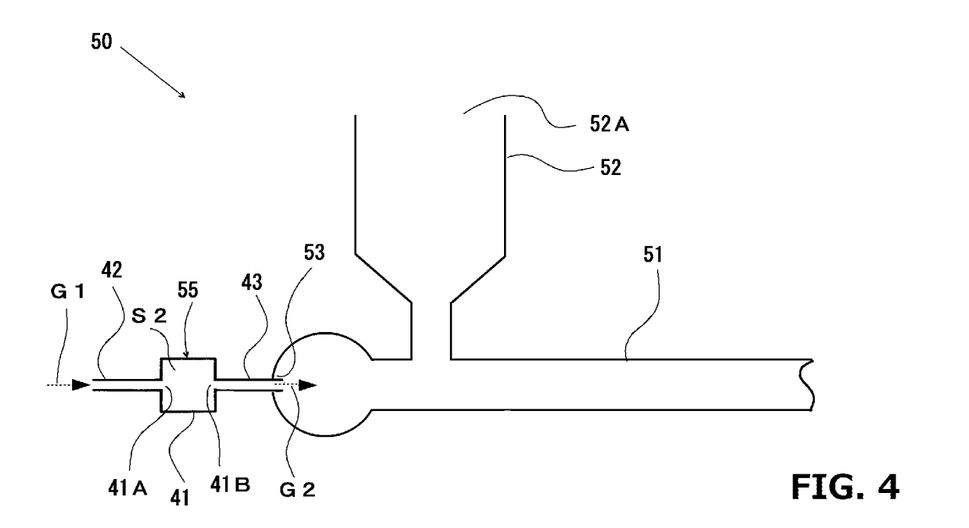
FIG. 4 is an explanatory view illustrating another example of a configuration of a processing mechanism used for implementing the processing method of the present invention.

Second Processing Mechanism:

FIG. 4 is an explanatory view illustrating another example of a configuration of a processing mechanism used for implementing the processing method according to the present invention.

In a second processing mechanism 50, a powdery moisture-phobic article is designated as a target object. The second processing mechanism 50 is a line-type processing mechanism that includes a conveying path formation member 51 that forms a conveying path for conveying the target object, and an ozone generator 55 that includes an ozone generation light source and feeds an ozone-containing gas to the conveying path. In the second processing mechanism 50, the conveying path formation member 51 is disposed to extend along a horizontal direction, and is connected to the ozone generator 55 through a gas feed opening 53 formed at an end thereof. A hopper 52 for storing the target object to be fed to the conveying path formed by the conveying path formation member 51 is provided on the side of one end of the conveying path formation member 51. The hopper 52 has an opening portion 52A that opens upward. In the second processing mechanism 50, the internal space of the conveying path formation member 51, i.e., the conveying path constitutes target object existing space. In the conveying path, processing is performed in a state of connecting the conveying path (the internal space of the conveying path formation member 51) and the outside (outside of the conveying path formation member 51) through the opening portion 52A.

In the illustrated example, a screw (not illustrated) for conveying the powdery moisture-phobic article (target object) in the horizontal direction (right direction of FIG. 4), while stirring the powdery moisture-phobic article, is disposed in the conveying path formation member 51.

The ozone generator 55 has the same configuration as that of the ozone generator 40 constituting the first processing mechanism 30 of FIG. 2, except that the ozone generator 55 is provided with humidity measurement means (not illustrated) and humidity adjustment means (not illustrated). In the ozone generator 55, the humidity measurement means measures the humidity (relative humidity) of an environmental gas constituting an environmental atmosphere of the second processing mechanism 50. The humidity adjustment means controls the humidity (relative humidity) of a gas (ozone-containing gas G2) ejected from the ozone generator 55 to be not more than 55% on the basis of a value of the humidity (relative humidity) measured by the humidity measurement means.

In the illustrated example, the humidity measurement means and the humidity adjustment means are disposed in an inlet path formation member 42 (ozone material gas inlet path). The humidity adjustment means may preferably be provided in the inlet path formation member 42 from the viewpoint of effective use of ozone. When the gas flowing through the ozone material gas inlet path (environmental gas constituting the environmental atmosphere of the second processing mechanism 50) has a low humidity and does not require dehumidification by the humidity adjustment means, the humidity adjustment means may be disposed in the outlet path formation member 43 (ozone-containing gas outlet path).

In the second processing mechanism 50 having such configuration, a sterilization process is performed on the target object (powdery moisture-phobic article) present in the conveying path (target object existing space) by the feeding gas control method of the processing method of the present invention.

More specifically, in the ozone generator 55, the ozone material gas feeding means feeds air (ambient air) constituting an environmental atmosphere of the second processing mechanism 50 as an ozone material gas G1 from the inlet path formation member 42 (ozone material gas inlet path) through the inlet 41A into the flow path formation member 41 (ozone generation space S2). The ozone material gas G1 fed to the inside of the flow path formation member 41 flows through the ozone material gas flow path to the outlet 41B, and is irradiated with the light (ozone generation light) from the excimer lamp 10 (ozone generation light source). Oxygen in the ozone material gas G1 absorbs the ozone generation light (ultraviolet rays), and so ozone is generated by ozone generation reaction. In this manner, the ozone-containing gas G2 that contains ozone generated by the irradiation of the ozone material gas G1 with the ozone generation light is ejected to the outside of the ozone generator 55 from the outlet path formation member 43 (ozone-containing gas outlet path) through the outlet 41B. The humidity adjustment means sets the relative humidity of the ozone-containing gas G2 ejected from the ozone generator 55 at not more than 55%.

In the conveying path to which the ozone-containing gas G2 is fed (the internal space of the conveying path formation member 51), in other words, in the target object existing space, the powdery moisture-phobic article is being conveyed.

In this manner, the target object present in the conveying path is exposed to the ozone-containing gas G2 fed from the ozone generator 55 to the conveying path at a low humidity condition, whereby the target object is subjected to a sterilization process. In the course of the process, the powdery moisture-phobic article is kept conveyed on the conveying path, and the conveying path is continuously kept fed with the ozone-containing gas G2.

In the processing method of the present invention performed by the processing mechanism, the target object is exposed to the ozone-containing gas, which is obtained by the irradiation of the ozone material gas with the ozone generation light. Therefore, the generated ozone is not decomposed due to the irradiation with the ozone generation light. As is apparent from the experiment example described later, the humidity (exposure relative humidity) of the gas (processing environmental gas) constituting the processing atmosphere does not largely interfere with a processing efficiency, in contrast to a processing method (sterilization and deodorization processing method) utilizing ozone generated by the discharge-system ozone generation method. More specifically, the processing method of the present invention can obtain a high processing efficiency even in a humidity condition in which the exposure relative humidity is not more than 55%, in which the processing method (sterilization and deodorization processing method) utilizing ozone generated by the discharge-system ozone generation method cannot obtain a high processing efficiency, in particular, in a humidity condition in which the exposure relative humidity is not more than 20%, in which a processing effect (a sterilization effect and a deodorization effect, in the concrete) cannot be obtained.

Accordingly, in the processing method of the present invention, a sterilization process and a deodorization process can be performed with high efficiency utilizing ozone without humidifying the target object. As a result, according to the processing method of the present invention, the moisture-phobic articles that should be kept as dry as possible (a low humidity condition having a relative humidity of the order of 0 to 50%, in the concrete), such as powdered food, dried food, spices and powdered medicines can be subjected to processing (sterilization process or deodorization process, in the concrete), without having the detrimental effects of quality deterioration, for example, impairment of flavor, fragrance and performance properties.

In the processing method according to the present invention, the concentration of ozone in the ozone-containing gas can be easily controlled by adjustment of an irradiation time of the ozone material gas with the ozone generation light.

In the processing method of the present invention, the concentration of ozone in the ozone-containing gas is, for example, not more than 50 ppm.

In the processing method of the present invention performed by the first processing mechanism 30 or the second processing mechanism 50, the ozone generator 40 or 55 is disposed outside the target object existing space, and the flow path formation member 41 of the ozone generator 40 or 55 blocks light from the ozone generation light source (excimer lamp 10). Therefore, since the target object is not irradiated with the light from the ozone generation light source (excimer lamp 10), the target object does not deteriorate due to the irradiation with the light (ultraviolet rays) from the ozone generation light source.

The processing method of the present invention has been described above in the concrete. However, the present invention is not limited to the above-described examples, but can be variously modified.

Figure 5:
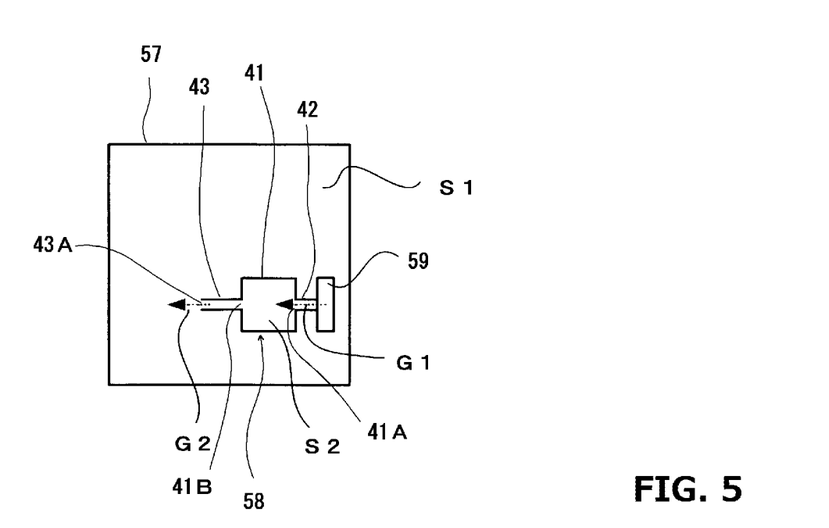
FIG. 5 is an explanatory view illustrating yet another example of a configuration of a processing mechanism used for implementing the processing method of the present invention.

For example, the processing mechanism used for performing the processing method of the present invention is not limited to the above configuration (the first processing mechanism 30 and the second processing mechanism 50, in the concrete). More specifically, for example, as shown in FIG. 5, a processing mechanism for performing the processing method of the present invention may be configured to feed an environmental gas (air, in the concrete) constituting an atmosphere of a processing space S1, i.e., a target object existing space, to an ozone generator 58 (the inside of a flow path formation member 41), as an ozone material gas G1. In the illustrated example, in the processing mechanism, the ozone generator 58 having an ozone generation light source is disposed in a case 57 that partitions the processing space S1. The ozone generator 58 has the same configuration as that of the ozone generator 40 constituting the first processing mechanism 30 of FIG. 2, except for using a unit configured to circulate the environmental gas (air) constituting the atmosphere of the processing space S1 (target object existing space) as ozone material gas feeding means 59. More specifically, the ozone material gas feeding means 59 can take the environmental gas constituting the atmosphere of the processing space S1, and feed the environmental gas into the flow path formation member 41 (ozone generation space S2) to cause the environmental gas to flow therethrough. In the processing mechanism having such configuration, the target object (powdery moisture-phobic article) present in the case 57 is subjected to processing by the atmospheric gas control method in the processing method of the present invention.

In the processing method of the present invention performed by the processing mechanism, as in the case of the processing method of the present invention performed by the first processing mechanism or the second processing mechanism, a sterilization process and a deodorization process can be performed with a high efficiency utilizing ozone without humidifying the target object. Even if the ozone generator 58 is disposed in the case 57 for containing the target object, the flow path formation member 41 of the ozone generator 58 blocks light from the ozone generation light source, and so the target object is not irradiated with the light from the ozone generation light source. Therefore, the target object does not deteriorate due to the irradiation with the light (ultraviolet rays) from the ozone generation light source.

Experiment examples of the present invention will be described below.

Figure 6:
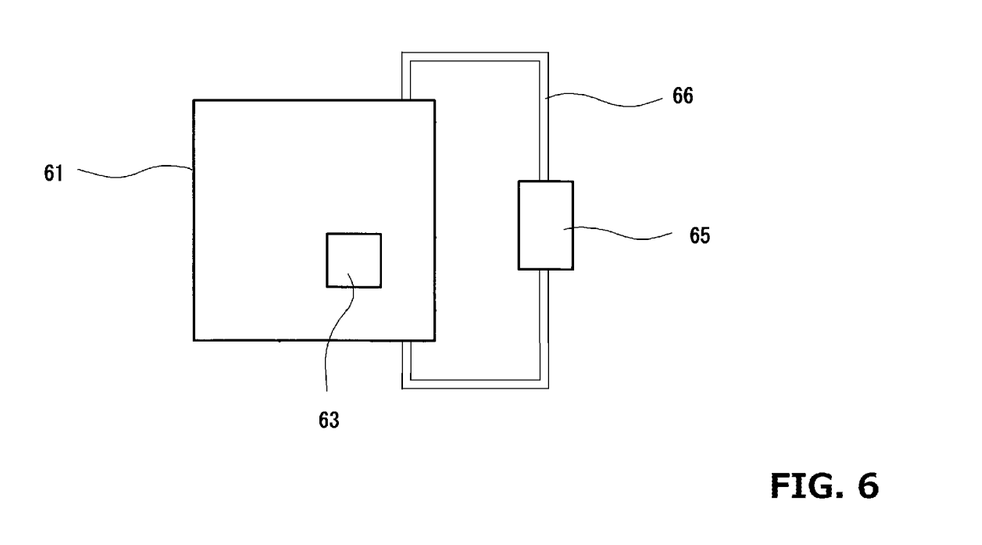
FIG. 6 is an explanatory view schematically illustrating a configuration of a processing mechanism used in an experiment example 1.

As shown in FIG. 6, an experimental processing mechanism (hereinafter also referred to as "experimental processing mechanism (1)") including an environment tester 61 having a volume of 288 L, an ozone generator 63 disposed in the environment tester 61 and an ozone monitor 65 connected to the environment tester 61 through a cyclic path formation member 66 was produced. In the ozone generator 63, a xenon excimer lamp (manufactured by USHIO Inc.) whose input power was 20 W, ultraviolet output was 4 W and emission light had a center wavelength of 172 nm was disposed in a right cylindrical flow path formation member made of stainless steel (SUS 316) along a tubular axis of the flow path formation member (refer to FIG. 3). In the ozone generator 63, since the flow path formation member was made of stainless steel and had a light-shielding property, light from the xenon excimer lamp was not emitted to the outside of the ozone generator 63. As the ozone monitor 65, an ultraviolet absorptive ozone monitor "EG-3000D" (made by EBARA JITSUGYO Co. Ltd.) was used. In the experimental processing mechanism (1), a gas (air) constituting an internal atmosphere of the environment tester 61 circulated through a cyclic path constituted of the cyclic path formation member 66, and the ozone monitor 65 measured the concentration of ozone in the air constituting the internal atmosphere.

The experimental processing mechanism (1) performed a sterilization process by a processing method of the present invention.

A comparative experimental processing mechanism (hereinafter also referred to as "experimental processing mechanism (2)") that used a discharge-system ozone generator "GO ONE 1000T (model number: GWD-1000T)" using input power (power consumption) of 45 W, as the ozone generator 63, in the experimental processing mechanism (1) was also produced.

The experimental processing mechanism (2) utilized, as an ozone generation method, a discharge system in which ozone was generated by silent discharge such as creeping discharge in an atmosphere of an ozone material gas (air, in the concrete). In the following description, a processing method using an ozone-containing gas obtained by the discharge-system ozone generation method performed by the experimental processing mechanism (2) was also referred to as "discharge-system using processing method".

Figure 7:
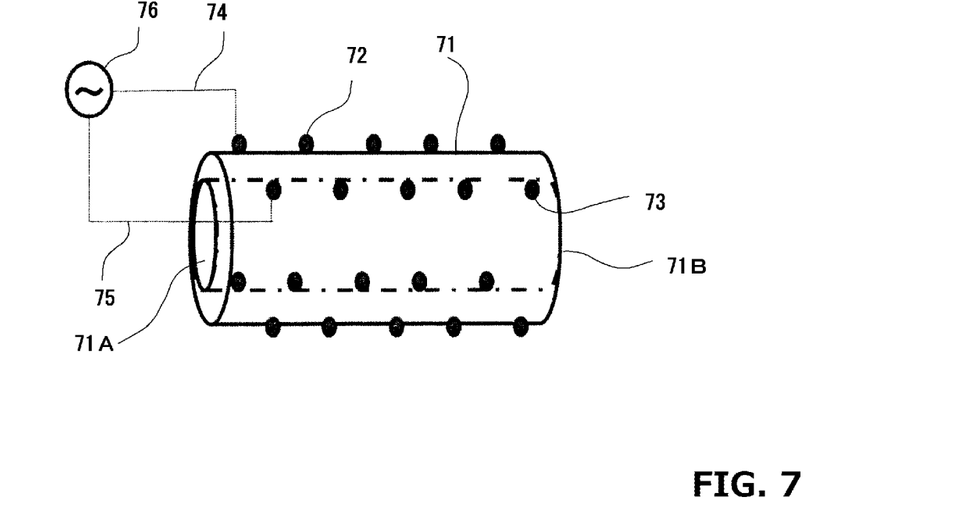
FIG. 7 is an explanatory view illustrating an essential portion of an ozone generator that constitutes a comparative experimental processing mechanism used in the experiment example 1.

As shown in FIG. 7, the ozone generator used in the discharge-system ozone generation method included, for example, a right cylindrical flow path formation member 71 made of dielectric material such as quartz glass. Air flowed from one end portion 71A to the other end portion 71B through columnar space partitioned by an inner periphery of the flow path formation member 71, and an air flow path in which discharge (silent discharge) occurred was formed in the columnar space. In the flow path formation member 71, one electrode 72 helically extending along a tubular axis was provided on an outer periphery thereof, and the other electrode 73 helically extending along the tubular axis was provided on an inner periphery. The electrodes 72 and 73 were connected to a high frequency power supply 76 through feeder lines 74 and 75, respectively.

A plurality of test section petri dishes and a plurality of comparison section petri dishes in which agar-based media were formed and *Escherichia coli* K12 (NBRC106373) was cultured in the agar-based media were prepared. In the test section petri dishes and the comparison section petri dishes, the number of the cultured *Escherichia coli* K12 (NBRC106373) (the number of colony forming units) was not lower than 1000 CFU and not more than 1200 CFU.

In the manufactured experimental processing mechanism (1) and experimental processing mechanism (2), the ozone generator 63 was continuously driven such that the concentration of ozone in the environment tester 61 became 40 ppm, on the condition that the relative humidity in the environment tester 61 was 5%, 10%, 20%, 30%, 40%, 50%, 55%, 60%, 70% or 80%. The inside of the environment tester 61 had a temperature of 20° C. and the same air pressure as atmospheric pressure. After a door (not illustrated) of the environment tester 61 was opened, the test section petri dishes were put in the environment tester 61, and the door was closed immediately. Due to the opening and closing of the door of the environment tester 61, the concentration of ozone inside the environment tester 61 was reduced to 30 ppm. After that, the drive of the ozone generator 63 was controlled (ON/OFF control) so as to keep the concentration of ozone in the environment tester 61 at 30±2 ppm. The inside of the environment tester 61 in a state that the concentration of ozone was kept at 30±2 ppm, the temperature and air pressure were constant. *Escherichia coli* K12 (NBRC106373) was exposed to the ozone-containing air having a concentration of ozone at 30±2 ppm.

After a lapse of an exposure time by which the CT value became 40, 60, 80 or 100, each test section petri dish was taken out of the environment tester 61. The test section petri dishes were left for 24 hours on the condition of a temperature of 37° C., together with the comparison section petri dishes.

Figure 8:
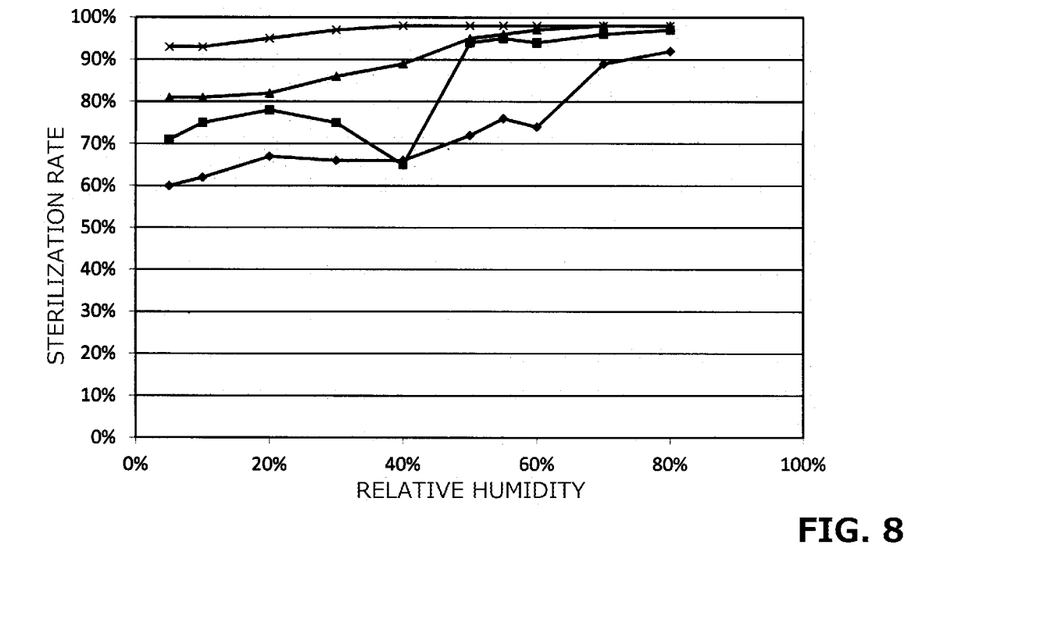
FIG. 8 is a graph showing the relationship between relative humidity and sterilization rate obtained by using an experimental processing mechanism in the experiment example 1.
Figure 9:
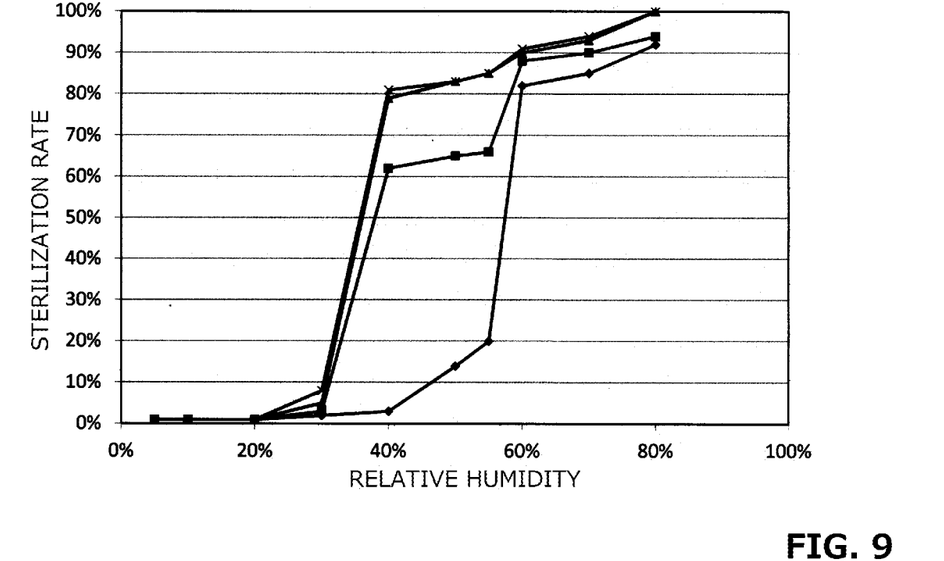
FIG. 9 is a graph showing the relationship between relative humidity and sterilization rate obtained by using a comparative experimental processing mechanism in the experiment example 1.

After the culture of 24 hours, the test section petri dishes and the comparison section petri dishes were checked, and the sterilization rate of *Escherichia coli* K12 (NBRC 106373) was calculated from the number of colonies, as to the test section petri dishes in which the number of colonies (the number of colony forming units) was less than 1000 CFU. Tables 1 and 2 and FIGS. 8 and 9 show the results. Table 1 and FIG. 8 show the results obtained by using the experimental processing mechanism (1), and Table 2 and FIG. 9 show the results obtained by using the experimental processing mechanism (2). In FIGS. 8 and 9, the results with a CT value of 40 are plotted with rhombuses (solid rhombus). The results with a CT value of 60 are plotted with rectangles (solid square). The results with a CT value of 80 are plotted with triangles (solid triangle). The results with a CT value of 100 are plotted with crosses (×).

In any of the comparison section petri dishes, the number of colonies (the number of colony forming units) was not less than 1000 CFU.

TABLE 1

| STERILIZATION RATE | | RELATIVE HUMIDITY | | | | | | | | | |
|---|---|---|---|---|---|---|---|---|---|---|---|
| | | 5% | 10% | 20% | 30% | 40% | 50% | 55% | 60% | 70% | 80% |
| CT VALUE | 40 | 60% | 62% | 67% | 66% | 66% | 72% | 76% | 74% | 89% | 92% |
| | 60 | 71% | 75% | 78% | 75% | 65% | 94% | 95% | 94% | 96% | 97% |
| | 80 | 81% | 81% | 82% | 86% | 89% | 95% | 96% | 97% | 98% | 98% |
| | 100 | 93% | 93% | 95% | 97% | 98% | 98% | 98% | 98% | 98% | 98% |

TABLE 2

| STERILIZATION RATE | | RELATIVE HUMIDITY | | | | | | | | | |
|---|---|---|---|---|---|---|---|---|---|---|---|
| | | 5% | 10% | 20% | 30% | 40% | 50% | 55% | 60% | 70% | 80% |
| CT VALUE | 40 | 1% | 1% | 1% | 2% | 3% | 14% | 20% | 82% | 85% | 92% |
| | 60 | 1% | 1% | 1% | 3% | 62% | 65% | 66% | 88% | 90% | 94% |
| | 80 | 1% | 1% | 1% | 5% | 79% | 83% | 85% | 90% | 93% | 100% |
| | 100 | 1% | 1% | 1% | 8% | 81% | 83% | 85% | 91% | 94% | 100% |

Figure 10:
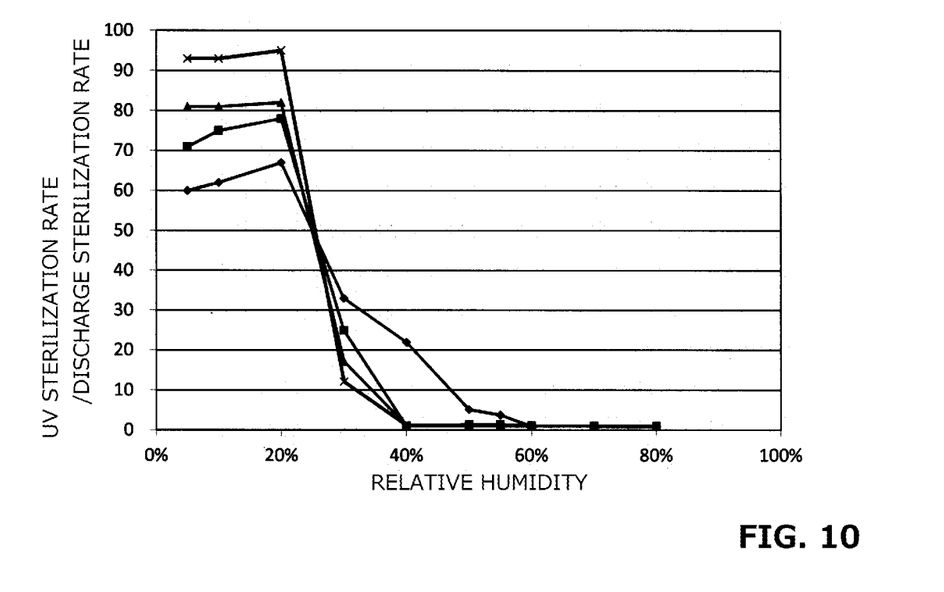
FIG. 10 is a graph showing the relationship between relative humidity and the ratio of the sterilization rate of the experimental processing mechanism relative to the sterilization rate of the comparative experimental processing mechanism.

On the basis of the results shown in Tables 1 and 2 and FIGS. 8 and 9, the ratio of the sterilization rate of the experimental processing mechanism (1), relative to the sterilization rate of the experimental processing mechanism (2), ("UV sterilization rate/discharge sterilization rate" in the graph of FIG. 10) was calculated in each of the cases in which the CT value was 40, 60, 80 and 100. Table 3 and FIG. 10 show the results. In FIG. 10, the results with a CT value of 40 are plotted with rhombuses (solid rhombus). The results with a CT value of 60 are plotted with rectangles (solid square). The results with a CT value of 80 are plotted with triangles (solid triangle). The results with a CT value of 100 are plotted with crosses (×).

TABLE 3

| UV/ DISCHARGE | | RELATIVE HUMIDITY | | | | | | | | | |
|---|---|---|---|---|---|---|---|---|---|---|---|
| | | 5% | 10% | 20% | 30% | 40% | 50% | 55% | 60% | 70% | 80% |
| CT VALUE | 40 | 60.0 | 62.0 | 67.0 | 33.0 | 22.0 | 5.1 | 3.8 | 1.0 | 1.0 | 1.0 |
| | 60 | 71.0 | 75.0 | 78.0 | 25.0 | 1.0 | 1.4 | 1.4 | 1.1 | 1.1 | 1.0 |
| | 80 | 81.0 | 81.0 | 82.0 | 17.2 | 1.1 | 1.1 | 1.1 | 1.1 | 1.1 | 1.0 |
| | 100 | 93.0 | 93.0 | 95.0 | 12.1 | 1.2 | 1.2 | 1.2 | 1.1 | 1.0 | 1.0 |

It is apparent from the results of the experiment example that the experimental processing mechanism (1) can obtain a high sterilization rate of 60% or more even if any type of air having a relative humidity of 5%, 10%, 20%, 30%, 40%, 50%, 55%, 60%, 70% or 80% was used as an ozone material gas. In particular, it is apparent that the experimental processing mechanism (1) can obtain a high sterilization rate even in the case of using air having a relative humidity of not more than 55% as an ozone material gas, though the experimental processing mechanism (2) cannot obtain a sterilization effect or a high sterilization rate with the use of the air.

Therefore, it was confirmed that the experimental processing mechanism (1) according to the present invention, in other words, the processing method of the present invention could process the target object with the high efficiency in the low humidity condition in which the relative humidity of the gas constituting the processing atmosphere was not more than 55%. In other words, it was confirmed that the target object could be processed with the high efficiency without humidifying the target object.

The same experiment as the experiment example described above was performed, except that an exposure time for which the *Escherichia coli* K12 (NBRC106373) cultured in the test section petri dishes was exposed to the ozone-containing gas was made constant and the concentration of ozone in the ozone-containing air was varied so as to have a CT value of 40, 60, 80 or 100. In the experiment, similar results to those obtained in the above-described experiment example were obtained.

In the above-described experiment example, the temperature of the inside of the environment tester was constant at 20° C. However, when the temperature of the inside of the environment tester is changed to, for example, 5° C., 10° C., 30° C., 40° C. or the like, similar results to those obtained in the above-described experiment example can be obtained.

The effects of the sterilization process by the processing method of the present invention are confirmed as described above, but it is conceivable that a deodorization process by the processing method of the present invention could also be performed with a high efficiency.

This is because ozone and radical, which contribute to inactivation of bacteria in the sterilization process, also contribute to decomposition of malodorous materials in the deodorization process.

REFERENCE SIGNS LIST 10 excimer lamp
11 arc tube
11A sealing portion
11B exhaust pipe butt end
14 internal electrode
15 internal lead
16 metal foil
17 external lead for internal electrode
18 external electrode
19 external lead for external electrode
21 base member
22, 23 feeder line
24 high frequency power supply
30 first processing mechanism
31 processing container
32 container body
33 lid member
34 gas feed opening
39 agitator
40 ozone generator
41 flow path formation member
41A inlet
41B outlet
42 inlet path formation member
43 outlet path formation member
50 second processing mechanism
51 conveying path formation member
52 hopper
52A opening portion
53 gas feed opening
55 ozone generator
57 case
58 ozone generator
59 ozone material gas feeding means
61 environment tester
63 ozone generator
65 ozone monitor
66 cyclic path formation member
71 flow path formation member
71A one end portion
71B the other end portion
72, 73 electrode
74, 75 feeder line
76 high frequency power supply
S1 processing space
S2 ozone generation space
G1 ozone material gas
G2 ozone-containing gas

The invention claimed is:

1. A processing method comprising:
   obtaining an ozone-containing gas by irradiating an ozone material gas with ozone generation light that does not include light in an ozone decomposition wavelength range and does include light having a wavelength of not more than 200 nm; and
   exposing a target object to the obtained ozone-containing gas to process the target object, wherein
   the target object is a moisture-phobic article,
   the target object is presented in a target object existing space constituted by a processing container or a target object existing space constituted by a conveying path for conveying the target object,
   the ozone-containing gas is provided to the target object existing space and the target object exposed to the ozone-containing gas to process the target object in a low humidity condition having the relative humidity of not more than 40%.

2. The processing method according to claim 1, wherein the ozone generation light is light emitted from a xenon excimer lamp.

3. The processing method according to claim 1, wherein the ozone-containing gas has a relative humidity of not more than 30%.

4. The processing method according to claim 1, wherein the ozone-containing gas has a relative humidity of not more than 20%.

5. The processing method according to claim 1, wherein an environmental gas constituting an atmosphere of the target object existing space in which the target object is present has a relative humidity of not more than 30%.

6. The processing method according to claim 1, wherein an environmental gas constituting an atmosphere of the target object existing space in which the target object is present has a relative humidity of not more than 20%.

7. The processing method according to claim 2, wherein the ozone-containing gas is fed into the target object existing space constituted by the conveying path through which the target object is conveyed, so that the target object is exposed to the ozone-containing gas in the conveying path.

8. The processing method according to claim 1, wherein the target object is exposed to the ozone-containing gas while stirring the target object.

* * * * *